United States Patent [19]
Nabai et al.

[11] Patent Number: 5,467,780
[45] Date of Patent: Nov. 21, 1995

[54] BIOPSY WOUND CLOSURE DEVICE AND METHOD

[76] Inventors: Hossein Nabai, 14555 Levan Rd. Suite 410, Livonia, Mich. 48154; Homayoon Rahbari, 1314 N. Macomb St., P.O. Box 360, Monroe, Mich. 48161

[21] Appl. No.: 358,815

[22] Filed: Dec. 19, 1994

Related U.S. Application Data

[62] Division of Ser. No. 56,399, May 4, 1993, Pat. No. 5,388,588.

[51] Int. Cl.$^6$ .................................................. A61B 5/00
[52] U.S. Cl. .............................................. 128/754; 604/11
[58] Field of Search .................................... 128/749, 753, 128/754, 759; 604/1, 11, 14, 15, 265; 606/108, 167, 170

[56] References Cited

U.S. PATENT DOCUMENTS

| | | | |
|---|---|---|---|
| 2,607,346 | 8/1952 | Milcent | 604/11 |
| 3,368,549 | 2/1968 | Ban et al. | 604/1 |
| 3,739,781 | 6/1973 | Patel | 604/11 |
| 3,890,204 | 6/1975 | Avery | 128/759 |
| 3,983,875 | 10/1976 | Truman | 604/11 |
| 4,895,559 | 1/1990 | Shippert | 604/15 |
| 5,007,895 | 4/1991 | Burnett | 604/11 |
| 5,080,655 | 1/1992 | Haaga | 604/265 |
| 5,203,767 | 4/1993 | Cloyd | 604/11 |

*Primary Examiner*—Max Hindenburg
*Attorney, Agent, or Firm*—Alex Rhodes

[57] ABSTRACT

A method and closure device for performing a routine biopsy procedure without the use of sutures or butterfly bandages. The method and closure device controls bleeding, repairs the biopsy site, reduces the likelihood of inducing excessive scarring and reduces the handling of tissue. The closure device is comprised of a circular sponge made from an absorbable foam material which swells and fills up the defect left by biopsy and an applicator for implanting the sponge into the biopsy site. The sponge is detachably held to one end of the applicator and is pre-cut to a diameter which approximately corresponds to the diameter of the punch which is used for excising a biopsy specimen. A fibrous cotton wad is attached to the other end of the applicator. After the specimen is excised the sponge is implanted into the space from which the specimen was taken. A slight pressure is applied to the sponge with the fibrous cotton wad for approximately 30 to 60 seconds to stop any excess bleeding.

13 Claims, 1 Drawing Sheet

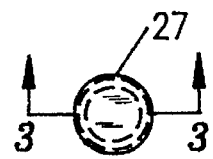
FIG. 1
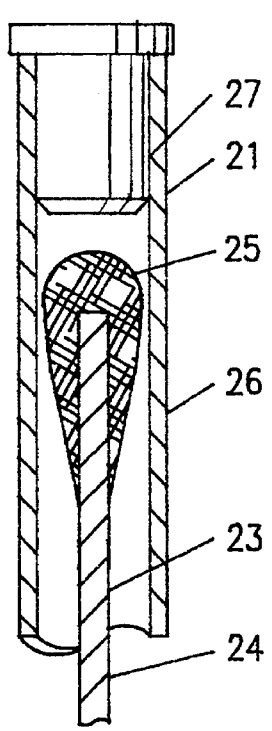
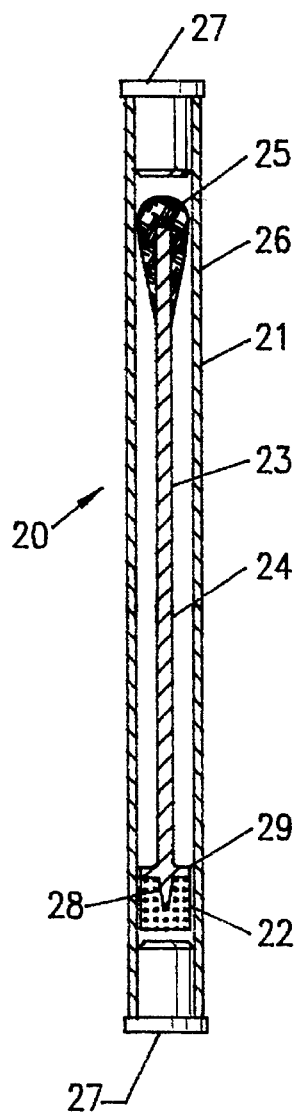
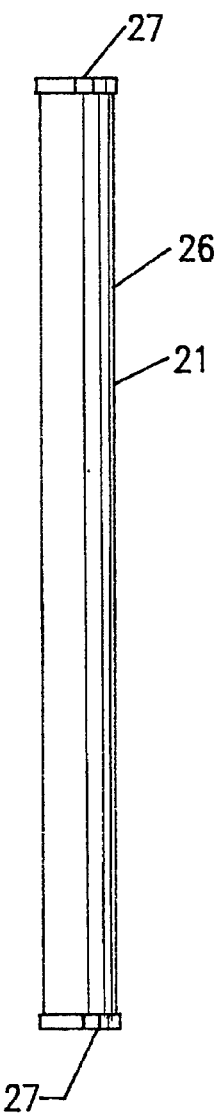
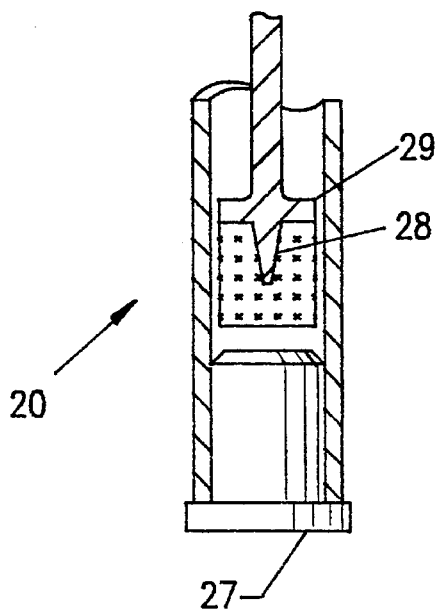
FIG. 4   FIG. 3   FIG. 2

BIOPSY WOUND CLOSURE DEVICE AND METHOD

This is a divisional of application Ser. No. 08/056,399 filed on May 4, 1993, now U.S. Pat. No. No. 5,388,588.

BACKGROUND OF THE INVENTION

This invention relates to wound closure devices and more particularly to a biopsy wound closure apparatus and method for controlling bleeding and repair of the biopsy site during a routine skin biopsy procedure.

The skin is a complex anatomical system composed of two layers—the epidermis, or epithelium, which is visible to the naked eye, and the dermis or corium, below the epidermis which is firmly interlocked with the dermis. When the skin is punctured, the cells of the surrounding dermis and epidermis multiply to compensate for the loss of cells in the dermis and epidermis. Skin biopsies are frequently performed to diagnose abnormal skin conditions.

Surgical punches, ranging in diameter from 2 to 6 millimeters, are commonly used to excise small samples of skin for medical biopsies. The punches are razor sharp circular knives which are pressed against the skin and rotated to excise cylinder shaped samples for biopsies. Surgical punches are illustrated in U.S. Pat. No. 5,388,588 which is incorporated herein by reference.

The current practice during a routine skin biopsy procedure is to use sutures, or for small wounds multiple butterfly bandages, to control the flow of blood and to repair the biopsy site. One deficiency with this practice is that some patients suffer anxiety during the suturing of wounds. Another deficiency is that a considerable amount of time is spent by physicians for hemostasis and repair of the biopsy site during routine biopsy procedures.

Sterile sponges have been used as packing material during surgery when hemostatic devices for controlling capillary, venous and arteriolar bleeding are either ineffective or impractical. However, sterile sponges have neither been available nor used to repair biopsy sites or to control bleeding during biopsy procedures. Nor have small pre-cut implant devices having the same or similar diameters as surgical punches been used to repair resulting defects or to control bleeding after excisions of specimens for skin biopsies.

In view of the foregoing, it is apparent that a more efficient, effective, easy to use apparatus and method for performing a routine biopsy procedure would satisy an existing need.

SUMMARY OF THE INVENTION

The present invention satisfies the existing need by providing a pre-cut sterile sponge and applicator for hemostasis and repair of a biopsy site during a routine biopsy procedure.

The invention is comprised of a pre-cut sterile sponge of the approximate shape and size of a specimen which is excised during a skin biopsy procedure and an applicator for inserting the sponge. The closure apparatus and method are effective for controlling bleeding, promoting healing, and reduce the likelihood of excessive scarring.

A further benefit, in the addition to the foregoing benefits, is that damage to the biopsy specimen is reduced because the biopsy procedure is performed with very little manipulation of the tissue.

In the first aspect of the invention, a porous pre-cut sponge is detachably held on one end of a slender applicator. At the other end of the applicator is a sterile wad of cotton fiber. After a biopsy specimen has been excised, the sterile sponge is implanted into the wound with the applicator, The foregoing features and benefits of our invention, together with other features and benefits, will be apparent from the ensuing detailed description taken in conjunction with the accompanying drawings. The best mode which is contemplated in practicing our invention is disclosed and the subject matter in which exclusive property rights are claimed is set forth in each of the numbered claims which are appended to the detailed description.

BRIEF DESCRIPTION OF THE DRAWINGS

FIG. 1 is a plan view of a closure device for a routine biopsy procedure which embodies the present invention.

FIG. 2 is a front elevational view of the closure device shown in FIG. 1.

FIG. 3 is a cross-sectional view taken on the line 3—3 in FIG. 1.

FIG. 4 is an enlarged fragmentary view of FIG. 3.

DETAILED DESCRIPTION OF THE PREFERRED EMBODIMENT

Referring now to the drawings wherein like numerals designate like and corresponding parts throughout the several views, in FIGS. 1 through 4, inclusive, is illustrated, for purposes of describing our invention, a closure device for repair of resulting skin defect and controlling bleeding during a routine skin biopsy procedure with reduction of chances of inducing excessive scar tissue.

The closure device, generally designated by the numeral 20, is housed in a sterile container 21 and is comprised of a pre-cut circular sponge 22 and an applicator 23 for implanting the sponge 22 into a bleeding site caused by the excising of a specimen of skin for a biopsy. The applicator is comprised of a slender rod 24 and a fibrous cotton wad 25 attached to one end of the rod 24. The sterile sponge 22 is loosely attached to the other end of said rod 24. The sterile container 21 is comprised of a cylindrical body 26 and a detachable cap 27 at each end of the body 27.

The sterile sponge 22 is pre-cut to diameters which correspond to diameters of conventional skin punches (not shown) by way of example, 2, 3, 4, 5 and 6 millimeters. The sponge 22 is a water-insoluble, porous item which is absorbed completely, with little tissue reaction. When the sponge 22 is implanted into the bleeding site, the sponge 22 absorbs blood, swells and terminates the flow of blood in the bleeding site and by filling up the biopsy site defect promotes healing without the necessity of approximation of the defect sides by suturing.

The applicator rod 24 is preferably made from a plastic material. The end of the rod 24 to which the sponge is loosely attached is tapered to facilitate the mounting of the sponge 22. Adjacent to the taper 28 there is a circular flange 29 for locating the sponge 22 on the rod 24 and to assist in implanting the sponge 22 into the bleeding site.

One material which has been evaluated and found to be acceptable for practicing our invention is an absorbable gelatin sponge manufactured by the Upjohn Company under the registered trademark "GELFOAM". It is a water-insoluble, off-white, non-elastic, porous, pliable product made from purified pork skin gelatin USP granules and is available in the form of pads.

The method for using our invention consists of the following steps. The biopsy area is cleaned and draped to provide a sterile environment. The skin is next anesthetized by an intradermal injection of a suitable anesthesiology material. A proper size sterile punch is pressed against the skin and rotated to excise specimens of epidermis and subcutaneous tissue for biopsy.

The closure device 20 having a sponge 22 whose diameter corresponds to the diameter of the excised area is removed from the sterile container 21. The sponge 22 is positioned and implanted with the applicator 23 into the bleeding site. The applicator 23 is removed from the sponge 22, the applicator 23 is inverted and pressure is applied with fiber cotton wad 25 for approximately 30 to 60 seconds to seal the wound and stop bleeding. For this and other embodiments described herein, a topical antibiotic ointment such as Bacitracin or Bactoroban is applied to the biopsy site and a conventional sterile dressing (not shown) is applied over the ointment. The dressing is removed after approximately 24 hours. The wound site may need to be cleaned twice a day with rubbing alcohol or a hydrogen peroxide solution until healing has been completed.

From the foregoing it will be understood that our invention provides an improved closure device and method for performing a routine biopsy procedure. Moreover, it will be appreciated that our improved closure device provides numerous benefits, among which are, a reduction in cost and time, reduced handling of tissue, and a reduction in the likelihood of inducing the formation of excessive scar tissue.

Although but several embodiments of our invention have been illustrated and described, it is not our intention to limit our invention to these embodiments since other embodiments can be provided by substitutions in materials and modifications in the shape, number and arrangements of parts and steps in our closure device and changes in steps in our method without departing from the spirit thereof.

We claim:

1. A closure device for the repair of skin tissue, controlling bleeding, and reducing the likelihood of inducing excess scar tissue during a routine skin biopsy procedure, comprising: a sterile tubular container for storing a close fitting pre-formed cylindrical sponge and an applicator for implanting said sponge in a bleeding site caused by the excising of a specimen of skin for a biopsy; a closely fitting pre-formed cylindrical sponge stored in the interior of said container, said sponge made from a foam material which swells and is absorbed in said bleeding site with little tissue reaction, said sponge being pre-formed to a diameter which is approximately equal to the diameter of a sharp circular blade of a surgical punch used for taking a specimen of skin for a biopsy from said biopsy site; a shard surgical punch for taking a specimen of skin from said biopsy site; and an applicator for extracting said sponge from said container and implanting said sterile sponge into said biopsy site after the excising of said specimen by said punch, said sponge being detachably held on to an end of said applicator; and a means at an opposite end of said applicator for applying pressure to said sponge for a short interval of time after said sponge has been implanted into said biopsy site.

2. The closure device recited in claim 1 wherein the diameter of said pre-formed cylindrical sponge is equal to the diameter of said circular blade of said punch.

3. The closure device recited in claim 1 wherein the diameter of said pre-formed cylindrical sponge is greater than the diameter of said circular blade of said punch.

4. The closure device recited in claim 1 wherein said sponge is a water-insoluble, non-elastic, porous and pliable product made from purified pork skin gelatin USP granules.

5. A closure device for the repair of skin tissue, controlling bleeding, and reducing the likelihood of inducing excess scar tissue, during a routine skin biopsy procedure, comprising: a sharp surgical punch having a diameter within a range of about 2 to 6 millimeters for taking a specimen of skin from said biopsy site; a pre-formed cylindrical sponge which is about the same diameter as the diameter of said circular blade of said punch used for excising said specimen of skin for said biopsy; and an applicator for implanting said sponge into a bleeding site caused by the excising of said specimen, said applicator having a rod, one end portion thereof being loosely attached to said sponge, and having a fibrous cotton wad, said wad being attached to an opposite end portion of said rod.

6. The closure device recited in claim 5 further comprising a sterile container for storing said sponge and said applicator, said sterile container comprising a tubular body having an inside diameter which is about equal to the diameter of said close fitting sponge; and at least one detachable cap slideably attached to an open end of said body.

7. A method for performing a skin biopsy procedure, said method comprising the steps of: implanting a pre-formed closely fitting sterile sponge detachably held on an end of an applicator into the space from which a biopsy specimen of epidermis and subcutaneous tissue has been excised with a cylindrical punch; applying pressure with a wad of fibrous cotton held on an opposite end of said applicator to said sterile sponge to control bleeding from said excised area.

8. The method recited in claim 7 wherein said pressure is applied to said sponge for 30 to 60 seconds.

9. The method recited in claim 7 further comprising the step of cleaning and draping said biopsy area before the excising of said specimen.

10. The method recited in claim 9 further comprising the step of anesthetizing the biopsy area by an intradermal injection of a suitable anesthesiology material after said biopsy area has been cleaned and draped.

11. The method recited in claim 7 further comprising the step of applying a topical antibiotic ointment to said sponge and the area surrounding said sponge after said bleeding has been controlled.

12. The method recited in claim 11 further comprising the step of applying a dressing over said excised area after said topical ointment has been applied.

13. The method recited in 12 further comprising the steps of removing said dressing and cleaning said excised area twice a day with rubbing alcohol or a hydrogen peroxide solution until healing has been completed.

\* \* \* \* \*

UNITED STATES PATENT AND TRADEMARK OFFICE
CERTIFICATE OF CORRECTION

PATENT NO. : 5,467,780
DATED : Nov. 21, 1995
INVENTOR(S) : Hossein Nabai and Homayoon Rahbari It is certified that error appears in the above-indentified patent and that said Letters Patent is hereby corrected as shown below:

Column 3, line 53, change "shard" to --sharp--

Column 4, line 56, after "recited in" insert --claim--

Signed and Sealed this

Twentieth Day of February, 1996

BRUCE LEHMAN

*Attest:*

*Attesting Officer*   Commissioner of Patents and Trademarks